United States Patent
Akbarali et al.

(10) Patent No.: US 9,994,523 B2
(45) Date of Patent: Jun. 12, 2018

(54) SALTS OF SAXAGLIPTIN WITH ORGANIC ACIDS

(71) Applicant: APOTEX INC., Toronto (CA)

(72) Inventors: Padiyath Mohammed Akbarali, Bangalore (IN); Venkata Ramana Kintali, Bangalore (IN); Shreenivasa Murthy H N, Bangalore (IN); Prakash Bhaskar Shetty, Bangalore (IN); Narendra Manjeshwar Mallya, Bangalore (IN); Venkataramana Lachhi Reddy, Bangalore (IN)

(73) Assignee: Apotex Inc., Toronto, Ontario (CA)

( * ) Notice: Subject to any disclaimer, the term of this patent is extended or adjusted under 35 U.S.C. 154(b) by 160 days.

(21) Appl. No.: 14/403,552

(22) PCT Filed: May 24, 2013

(86) PCT No.: PCT/IB2013/001031
§ 371 (c)(1),
(2) Date: Nov. 24, 2014

(87) PCT Pub. No.: WO2013/175297
PCT Pub. Date: Nov. 28, 2013

(65) Prior Publication Data
US 2015/0353490 A1    Dec. 10, 2015

Related U.S. Application Data

(60) Provisional application No. 61/668,537, filed on Jul. 6, 2012.

(30) Foreign Application Priority Data

May 24, 2012    (IN) .......................... 1572/MUM/2012

(51) Int. Cl.
*C07D 209/52*     (2006.01)
*C07C 65/05*      (2006.01)
*C07D 213/80*     (2006.01)

(52) U.S. Cl.
CPC ............ *C07D 209/52* (2013.01); *C07C 65/05* (2013.01); *C07D 213/80* (2013.01); *C07B 2200/13* (2013.01)

(58) Field of Classification Search
USPC ......................................................... 548/452
See application file for complete search history.

(56) References Cited

U.S. PATENT DOCUMENTS

| 6,395,767 B2 | 5/2002 | Robl et al. |
| 7,214,702 B2 | 5/2007 | Sharma |
| 2005/0090539 A1 | 4/2005 | Vu et al. |
| 2008/0279932 A1* | 11/2008 | Reber .................. C07D 207/16 424/464 |
| 2009/0054303 A1 | 2/2009 | Gougoutas et al. |
| 2010/0124541 A1 | 5/2010 | Gant et al. |

FOREIGN PATENT DOCUMENTS

| CN | 102086172 A | 6/2011 |
| WO | 0168603 A2 | 9/2001 |
| WO | 2004052850 A2 | 6/2004 |
| WO | 2008131149 A2 | 10/2008 |
| WO | WO 2008131149 A2 * | 10/2008 |
| WO | 2010115974 A1 | 10/2010 |
| WO | 2011140328 A1 | 11/2011 |
| WO | 2012017028 A1 | 2/2012 |
| WO | 2012017029 A1 | 2/2012 |
| WO | 2013160354 A1 | 10/2013 |
| WO | 2014002114 A2 | 1/2014 |
| WO | 2014006569 A2 | 1/2014 |

OTHER PUBLICATIONS

Savage et al., "Preparation of Saxagliptin, a Novel DPP-IV Inhibitor", Organic Process Research & Development, 2009, pp. 1169-1176, 13(6).
"Saxagliptin Hydrochoride Acetic Acid Cocrystal", IP.com Journal, (2013), 14(1A), 1 page (IPCOM000233597d).
Bighley, "Salt Forms of Drugs and Absorption" in Encyclopedia of Pharmaceutical Technology; Marcel Dekker, Inc.: New York; 1996; pp. 453-499.

* cited by examiner

*Primary Examiner* — Charanjit Aulakh
(74) *Attorney, Agent, or Firm* — The Webb Law Firm

(57) ABSTRACT

The invention relates to organic salts of Saxagliptin and processes for their preparation.

25 Claims, 6 Drawing Sheets

SALTS OF SAXAGLIPTIN WITH ORGANIC ACIDS

TECHNICAL FIELD

The invention relates to salts of Saxagliptin with organic acids (HA) represented by formula (I). The present invention also relates to the methods of making the salts of Saxagliptin with organic acids.

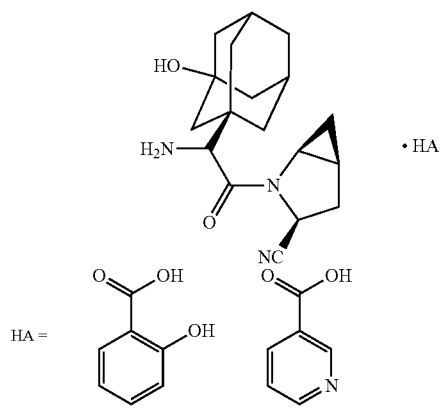

(I)

BACKGROUND

Saxagliptin [(1S,3S,5S)-2-[(2S)-2-amino-2-(3-hydroxy-1-adamantyl) acetyl]-2-azabicyclo[3.1.0]hexane-3-carbonitrile] and its hydrochloride salt are orally active reversible dipeptidyl peptidase-4 (DPP4) inhibitors, which are used as therapeutic agents for the treatment of type-2-diabetes mellitus, obesity, or related diseases. It is disclosed in example 60 of U.S. Pat. No. 6,395,767.

PCT application WO 2001068603 A2 discloses Saxagliptin in the form of its trifluoroacetate salt, as described in Example 60.

The processes for the preparation of Saxagliptin benzoate salt (scheme VII, Example 41), Saxagliptin free base and free base monohydrate (Example 42), and Saxagliptin hydrochloride (scheme VIIB, Example 42) are disclosed in the PCT application WO 2004052850 A2.

WO 2008131149 A2 discloses Saxagliptin free base, specific acid addition salts of Saxagliptin such as hydrochloride, hydrobromide, hydroiodide, ammonium sulfate, nitrate, benzoate, tartrate, fumarate and trifluoroacetate salts, and certain polymorphs, and hydrates thereof.

Methods of preparation of Saxagliptin hydrochloride are described in U.S. Pat. No. 7,214,702 B2 and in Organic Process Research & Development 2009, 13(6), 1169-1176.

PCT application WO 2010115974 A1 describes certain polymorphic forms of Saxagliptin hydrochloride.

CN 102086172 A discloses mesylate, maleate, malate, succinate and citrate salts of Saxagliptin.

PCT application WO 2012017028 A1 describes the phosphoric acid salt of Saxagliptin and its polymorphic forms.

PCT application WO 2012017029 A1 discloses crystalline forms of Saxagliptin salts with organic diacids such as form A of Saxagliptin maleate, form B of Saxagliptin L-malate, and form C of Saxagliptin succinate.

SUMMARY

The invention is based, at least in part, on salts of Saxagliptin with organic acids (HA) represented by formula I. The present invention is also based, at least in part, on methods of making the salts of Saxagliptin with organic acids. The salts of the present invention may exhibit good filtration characteristics and may be isolated with high purity.

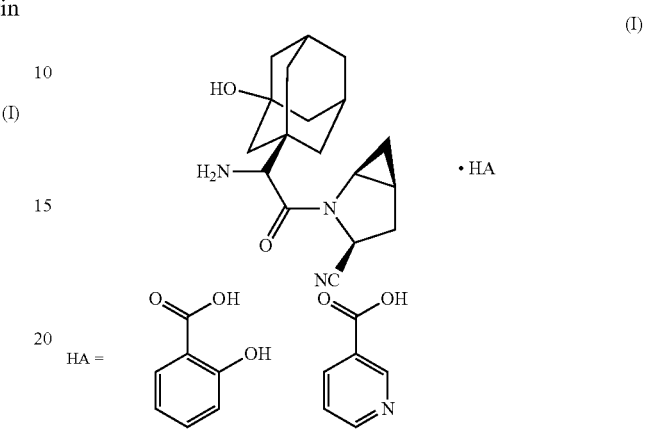

(I)

Provided are the compounds of formula Ia and Ib:

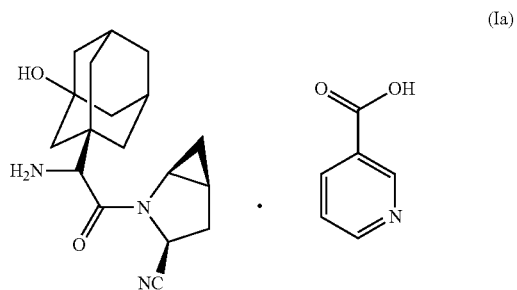

(Ia)

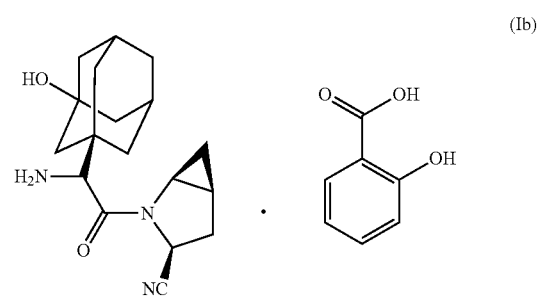

(Ib)

The nicotinate salt (compound of formula Ia) and the salicylate (compound of formula Ib), are suitable for use as intermediates in the isolation of Saxagliptin in high purity and to prepare other pharmaceutically acceptable salts such as the hydrochloride. They may also be useful in Saxagliptin compositions.

In illustrative embodiments, there is provided, a salt of Saxagliptin of formula (I):

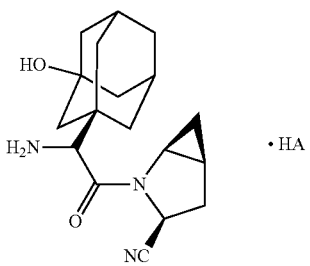

(I)

wherein HA is

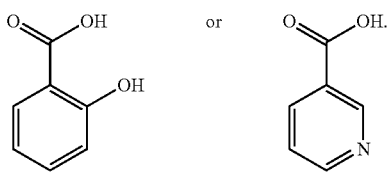 [SMILES: O=C(O)c1ccccc1O ; O=C(O)c1cccnc1]

In illustrative embodiments, there is provided a salt of Saxagliptin described herein wherein the salt is crystalline.

In illustrative embodiments, there is provided as Saxagliptin nicotinate of formula (Ia):

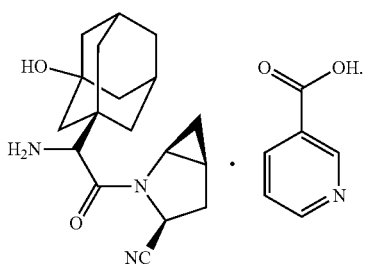

(Ia)

In illustrative embodiments, there is provided a Saxagliptin nicotinate (Ia) described herein in a crystalline monohydrate form.

In illustrative embodiments, there is provided a Saxagliptin nicotinate (Ia) described herein characterized by a XRPD diffractogram having peaks, expressed in degrees 2 theta, at approximately 7.3, 10.9, 16.3, 19.2, and 20.6.

In illustrative embodiments, there is provided a Saxagliptin nicotinate (Ia) described herein characterized by a XRPD diffractogram substantially similar to the XRPD diffractogram in FIG. 1.

In illustrative embodiments, there is provided a Saxagliptin nicotinate (Ia) described herein characterized by a DSC thermogram having two endothermic peaks with peak maxima at approximately 88° C. and approximately 235° C. and two exothermic peaks with peak maxima at approximately 140° C. and approximately 160° C.

In illustrative embodiments, there is provided a Saxagliptin nicotinate (Ia) described herein characterized by a DSC thermogram substantially similar to the DSC thermogram in FIG. 3.

In illustrative embodiments, there is provided a Saxagliptin nicotinate (Ia) described herein characterized by an IR spectrum having one or more adsorption peaks, expressed in cm$^{-1}$, at approximately 3336, 3046, 2134 and 1647.

In illustrative embodiments, there is provided a Saxagliptin nicotinate (Ia) described herein characterized by an IR spectrum substantially similar to the IR spectrum in FIG. 5.

In illustrative embodiments, there is provided a Saxagliptin salicylate of formula (Ib):

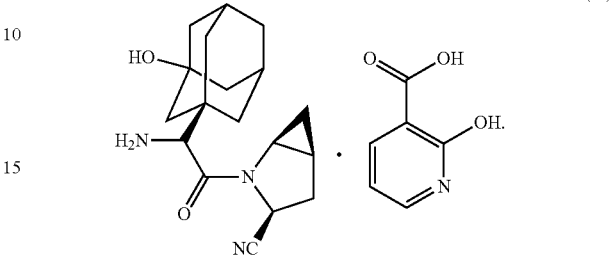

(Ib)

In illustrative embodiments, there is provided a Saxagliptin salicylate (Ib) described herein in an anhydrous crystalline form.

In illustrative embodiments, there is provided a Saxagliptin salicylate (Ib) described herein characterized by a XRPD diffractogram having peaks, expressed in degrees 2 theta, at approximately 6.7, 8.4, 13.4, 15.1, 17.5, and 21.1.

In illustrative embodiments, there is provided a Saxagliptin salicylate (Ib) described herein characterized by a XRPD diffractogram substantially similar to the XRPD diffractogram in FIG. 2.

In illustrative embodiments, there is provided a Saxagliptin salicylate (Ib) described herein characterized by a DSC thermogram having an exothermic peak with a peak maximum at approximately 210° C. and an endothermic peak with a peak maximum at approximately 263° C.

In illustrative embodiments, there is provided a Saxagliptin salicylate (Ib) described herein characterized by a DSC thermogram substantially similar to the DSC thermogram in FIG. 4.

In illustrative embodiments, there is provided a Saxagliptin salicylate (Ib) described herein characterized by an IR spectrum having one or more adsorption peaks, expressed in cm$^{-1}$, at approximately 3584, 3455, 3041.8, 2112, 1669 and 1630.

In illustrative embodiments, there is provided a Saxagliptin salicylate (Ib) described herein characterized by an IR spectrum substantially similar to the IR spectrum in FIG. 6.

In illustrative embodiments, there is provided a process for the preparation of salts of Saxagliptin of formula I:

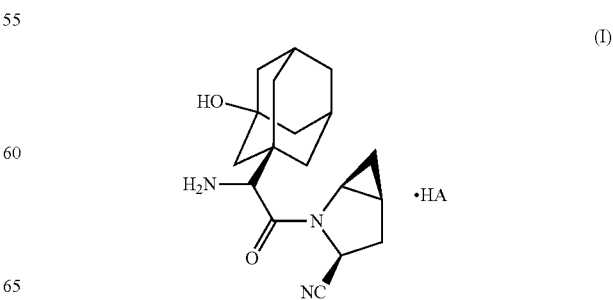

(I)

wherein HA is

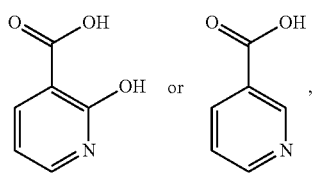 [SMILES: O=C(O)c1cccnc1O ; O=C(O)c1cccnc1]

the process comprising: (a) treating, at a temperature of about 40° C. to about 65° C., (S)—N-Boc-3-hydroxyadamantylglycine-L-cis-4,5-methanoprolinenitrile with either: (i) a mineral acid in water or (ii) a mixture of water and an alcoholic solvent, thereby forming a solution; (b) adding a water-immiscible solvent to the solution, thereby forming a bi-phasic solution; (c) basifying the bi-phasic solution by adjusting the pH to about 9 to about 9.5, thereby forming a basified bi-phasic solution; (d) separating an organic phase from the basified bi-phasic solution; (e) treating the organic phase with an organic acid, thereby forming a treated organic phase; and (f) isolating the salt of Saxagliptin from the treated organic phase.

In illustrative embodiments, there is provided a process described herein wherein the mineral acid is hydrochloric acid.

In illustrative embodiments, there is provided a process described herein wherein the alcoholic solvent is a $C_1$-$C_3$ alkanol selected from the group consisting of methanol, ethanol, and isopropanol.

In illustrative embodiments, there is provided a process described herein wherein the water-immiscible solvent is dichloromethane or ethyl acetate.

In illustrative embodiments, there is provided a process described herein wherein the organic acid is selected from the group consisting of nicotinic acid and salicylic acid.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
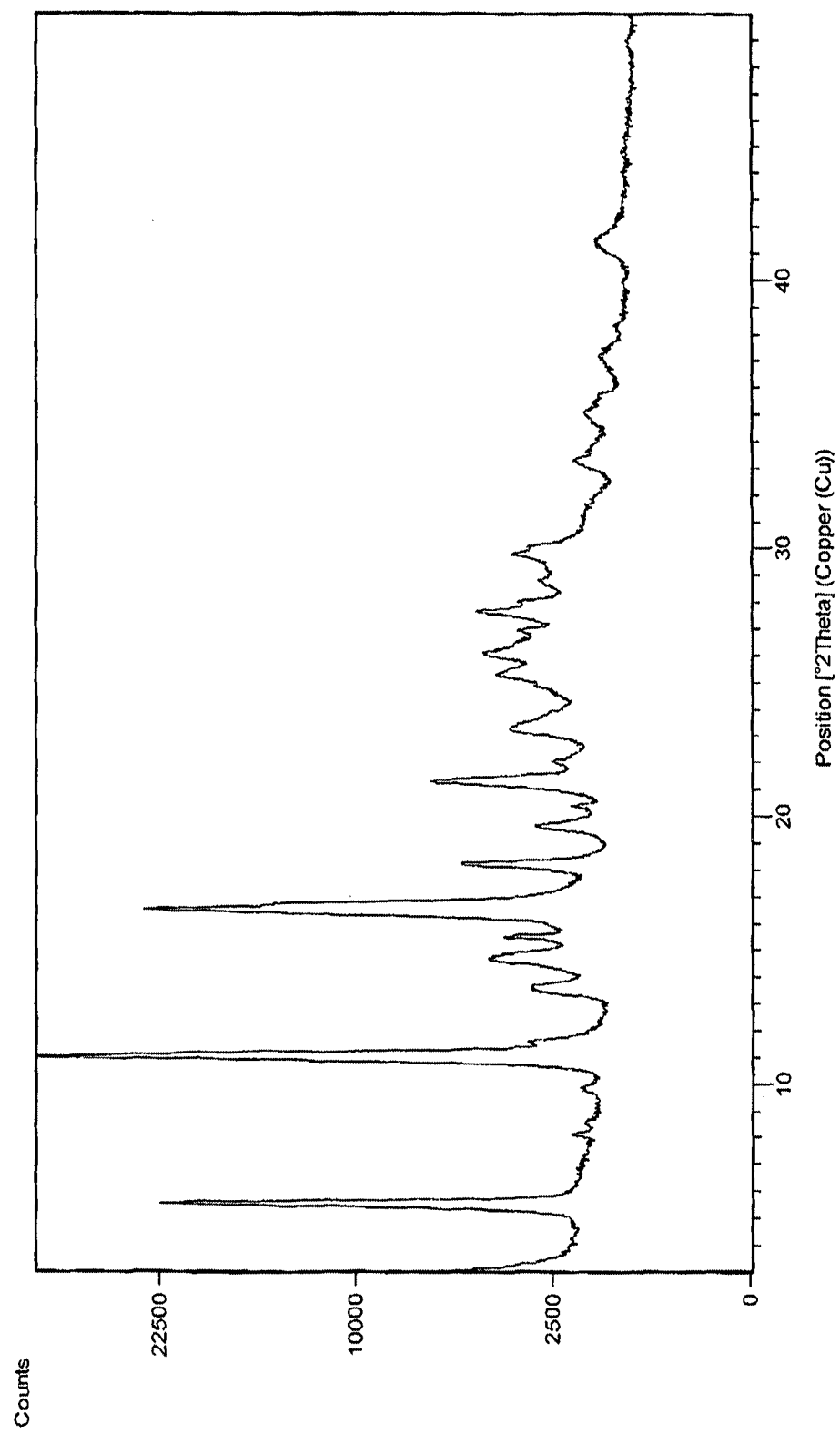
FIG. 1: is a X-ray powder diffraction pattern (XRPD) of Saxagliptin nicotinate as per Example 1.

When used in reference to a spectrum and/or data presented in a graph, the term "substantially" should be interpreted as encompassing a diffractogram within acceptable boundaries of experimentation.

When used in reference to a peak in the XRPD diffractogram, the term "approximately" generally means that the peak is within plus or minus 0.2 degrees 2 theta of the quoted value.

When used in reference to a peak in the FTIR spectrum, the term "approximately" generally means that the peak is within plus or minus 5 $cm^{-1}$ of the quoted value.

When used in reference to a peak in the DSC thermogram, the term "approximately" generally means that the peak is within plus or minus 2 degrees of the quoted value.

As used herein when referring to a spectrum and/or to data presented in a graph, the term "peak" refers to a feature that one skilled in the art would recognize as not attributable to background noise.

Depending on the nature of the methodology applied and the scale selected to display results obtained from X-ray diffraction analysis, the peak intensities of peaks obtained may vary quite dramatically. For example, it is possible to obtain a relative peak intensity of 0.01% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied The present invention encompasses the salts isolated in pure form or when admixed with other materials, for example other isomers and/or polymorphic forms and/or salt forms or any other material.

Hydrates have some variability in the exact molar ratio of their components depending on a variety of conditions understood to a person of skill in the art. For example, a molar ratio of components within a solvate provides a person of skill in the art information as to the general relative quantities of the components of the solvate and in many cases the molar ratio may vary by about plus or minus 20% from a stated range. For example, a molar ratio of 1:1 is understood to include the ratio 1:0.8 as well as 1:1.2 as well as all of the individual ratios in between.

Saxagliptin in the form of the salts with either nicotinic acid or salicylic acid is easier to isolate in high purity than the free base. These salt-forms reduce the propensity of the molecule to undergo decomposition. Saxagliptin is known to undergo intramolecular cyclization to produce the cyclic amidine impurity (compound of formula A) (*Organic Process Research & Development* 2009, 13, 1169-1176 (page 1173) and WO 2011/140328 A1 (page 29)) during crystallization and upon storage.

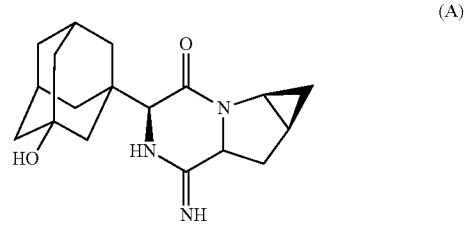

(A)

In one embodiment, the present invention provides a salt of Saxagliptin represented by formula (I).

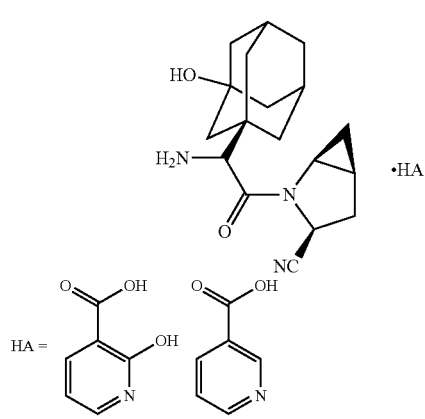

In another embodiment, there is provided a Saxagliptin nicotinate salt of formula (Ia),

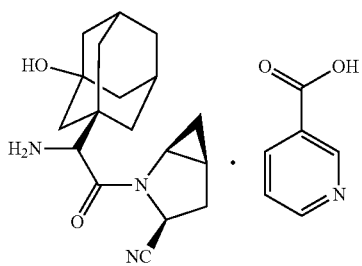

Saxagliptin nicotinate of formula (Ia) has a crystalline nature and is found to be a monohydrate as indicated by a water content of about 4.3% as measured by the Karl-Fischer method.

An illustrative XRPD diffractogram of Saxagliptin nicotinate of formula (Ia) acquired according to the conditions given in Example 4 is shown in FIG. 1. According to FIG. 1, the Saxagliptin nicotinate of formula (Ia) may have a reflection ("peak") at any one or more of the following values expressed in degrees 2θ at approximately 7.3, 10.9, 16.3, 19.2, and 20.6.

Figure 5:
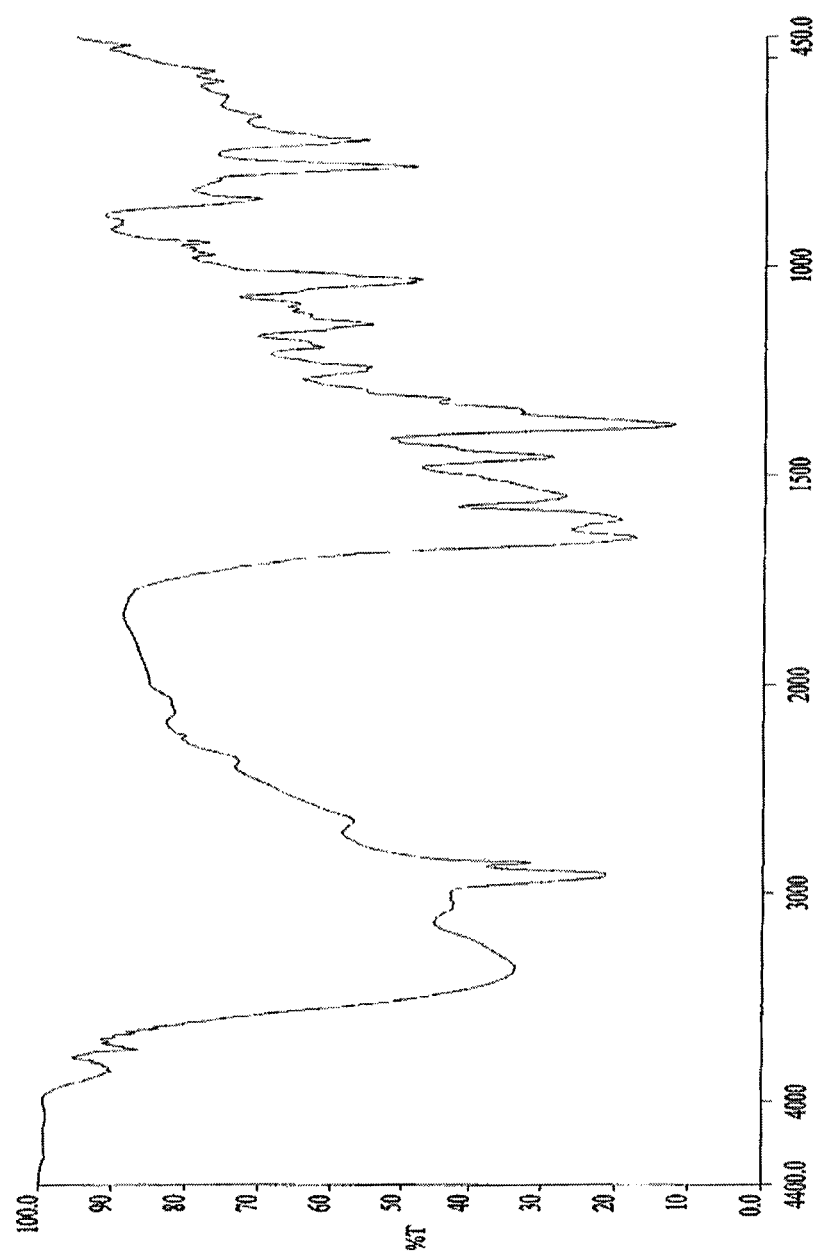
FIG. 5: is an IR absorption spectrum of Saxagliptin nicotinate as per Example 1.

An illustrative FTIR spectrum of the Saxagliptin nicotinate of formula (Ia) acquired according to the conditions given in Example 5 is shown in FIG. 5. According to FIG. 5, the Saxagliptin nicotinate of formula (Ia) may have an absorption band ("peak") at any one or more of the following values expressed in $cm^{-1}$ of approximately 3336, 3046, 2134 and 1647.

Figure 3:
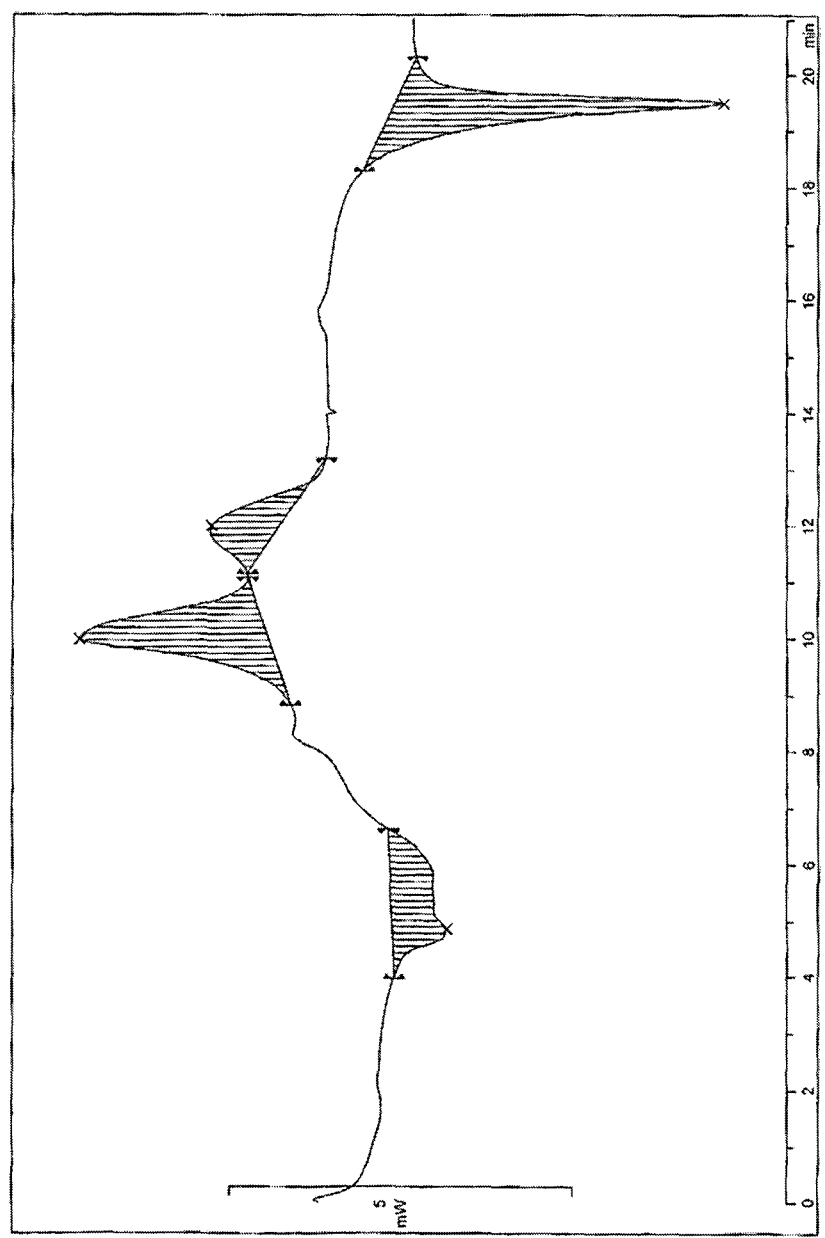
FIG. 3: is a DSC of Saxagliptin nicotinate as per Example 1.

An illustrative DSC thermogram of Saxagliptin nicotinate of formula (Ia) acquired according to the conditions given in Example 6 is shown in FIG. 3. The DSC thermogram shown in FIG. 3 may be illustrative of the type of results obtained when analysing Saxagliptin nicotinate of formula (Ia) by DSC. The DSC thermogram may be further characterized by two endothermic peaks with peak maxima at approximately 88° C. and approximately 235° C. and two exothermic peaks with peak maxima at approximately 140° C. and approximately 160° C.

In another embodiment, there is provided a Saxagliptin salicylate salt of formula (Ib),

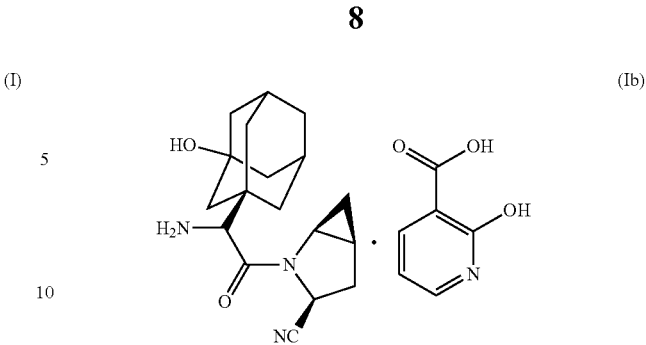

Saxagliptin salicylate of formula (Ib) has a crystalline nature and is essentially anhydrous as indicated by a water content of not more than approximately 0.5% as measured by the Karl-Fischer method.

Figure 2:
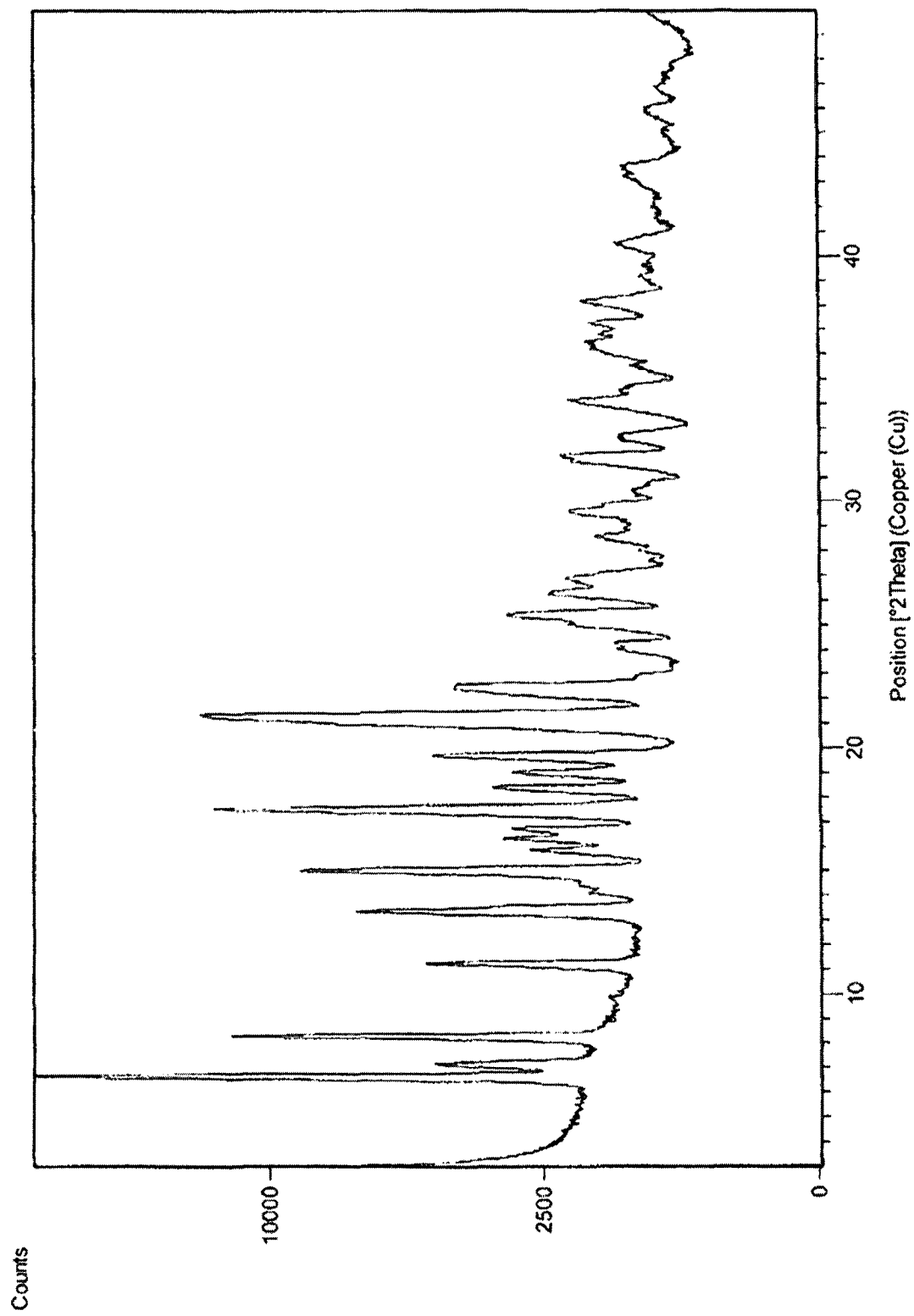
FIG. 2: is a X-ray powder diffraction pattern of Saxagliptin salicylate as per Example 3.

An illustrative XRPD diffractogram of Saxagliptin salicylate salt of formula (Ib) acquired according to the conditions given in Example 4 is shown in FIG. 2. According to FIG. 2, the Saxagliptin salicylate salt of formula (Ib) may have a reflection ("peak") at any one or more of the following values expressed in degrees 2 theta at approximately 6.7, 8.4, 13.4, 15.1, 17.5, and 21.1.

Figure 6:
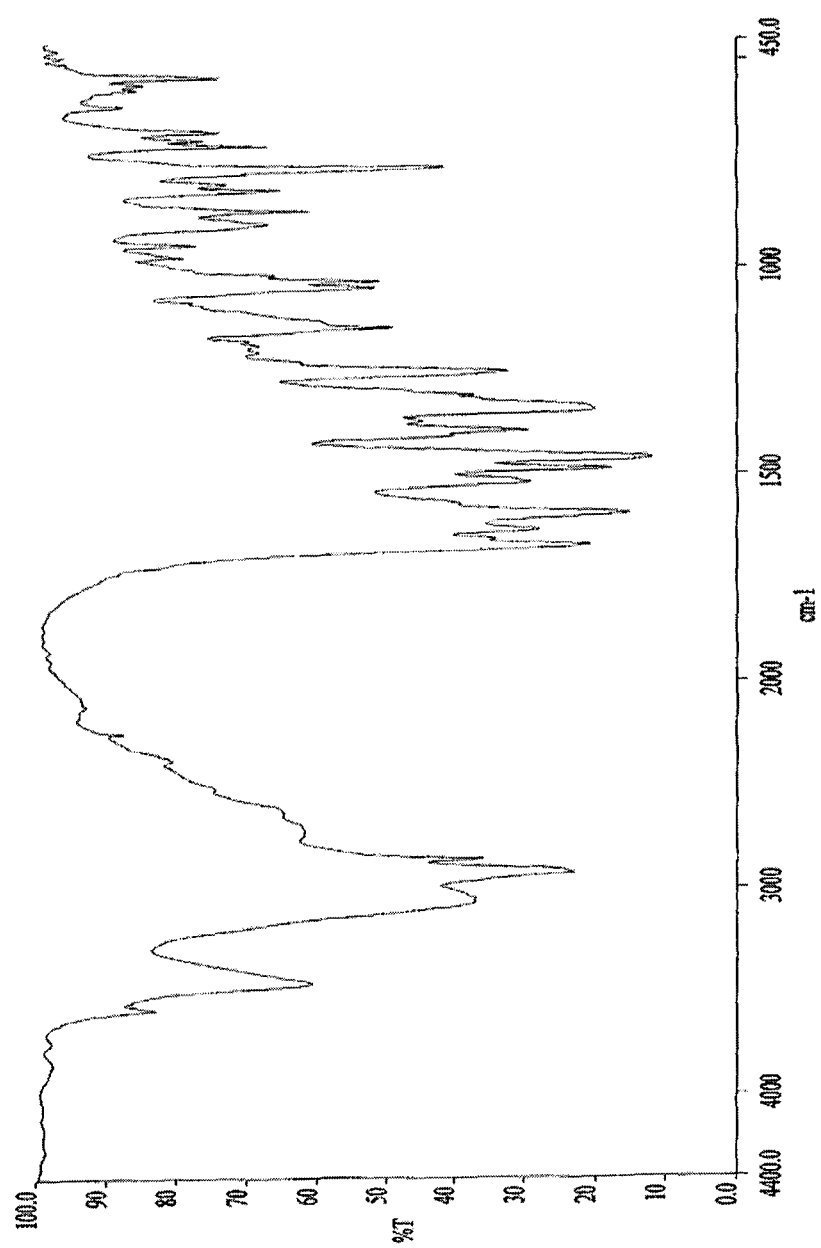
FIG. 6: is an IR absorption spectrum of Saxagliptin salicylate as per Example 3.

An illustrative FT spectrum of the Saxagliptin salicylate salt of formula (Ib) acquired according to the conditions given in Example 5 is shown in FIG. 6. According to FIG. 6, the Saxagliptin salicylate salt of formula (Ib) may have an absorption band ("peak") at any one or more of the following values expressed in $cm^{-1}$ of approximately 3584, 3455, 3041.8, 2112, 1669 and 1630.

Figure 4:
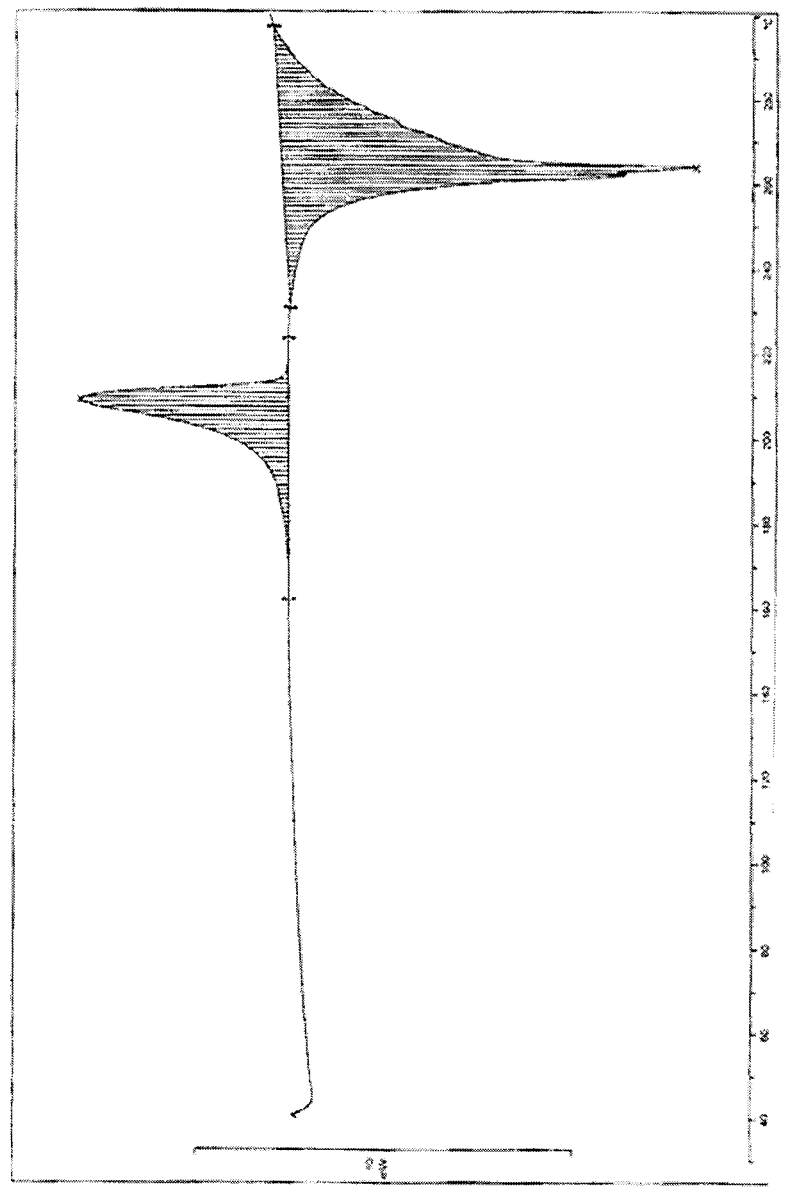
FIG. 4: is a DSC of Saxagliptin salicylate as per Example 3.

An illustrative DSC thermogram of Saxagliptin salicylate salt of formula (Ib) acquired according to the conditions given in Example 6 is shown in FIG. 4. The DSC thermogram shown in FIG. 4 may be illustrative of the type of results obtained when analysing Saxagliptin salicylate salt of formula (Ib) by DSC. The DSC thermogram may be further characterized by an exothermic peak with a peak maximum at approximately 210° C. and an endothermic peak with a peak maximum at approximately 263° C.

In an embodiment of the present invention, there is provided a process for the preparation of salts of Saxagliptin of formula (I):

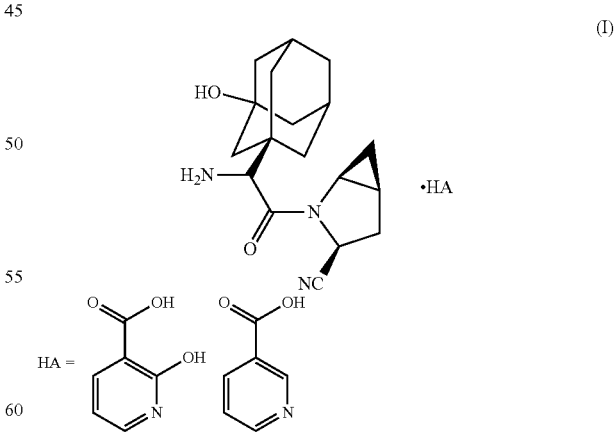

comprising:
a) treating(S)—N-Boc-3-hydroxyadamantylglycine-L-cis-4,5-methanoprolinenitrile (II) with a mineral acid in water or a mixture of water and an alcoholic solvent at a temperature of about 40° C. to about 65° C., b) adding a water-immiscible solvent,
c) basifying the bi-phasic solution containing Saxagliptin free base by adjusting the pH to 9 to 9.5,
d) separating the organic phase,
e) treating the organic phase with an organic acid, and
f) isolating the organic acid salt of Saxagliptin.

The mineral acid used in step (a) may be selected from the group consisting of HCl or $H_2SO_4$. In an embodiment, the mineral acid is HCl.

The alcoholic solvent may be selected from the group consisting of $C_1$-$C_3$ alkanols such as methanol, ethanol, and isopropanol. In an embodiment, the alcoholic solvent is isopropanol.

The water-immiscible solvent in step (b) may be dichloromethane or ethyl acetate.

The organic acids used for the preparation of salts of Saxagliptin are nicotinic acid and salicylic acid. The organic acid used is about 1 to 1.1 equivalents relative to Saxagilptin.

In illustrative embodiments of the present invention, the salts of the invention may be prepared by an exemplary process as set out in Scheme 1. Exemplary reagents and conditions for these reactions are disclosed herein.

Example 1: Preparation of Saxagliptin Nicotinate (Ia)

To a well-stirred mixture of 5 g of (S)—N-Boc-3-hydroxyadamantylglycine-L-cis-4,5-methanoprolinenitrile (II) in water (5 mL) was added isopropyl alcohol (5 mL) at 30° C., followed by 1.4 equivalents of conc. HCl, and the reaction mixture was heated to 60-65° C. The reaction mass was maintained at this temperature for 1.5-2 h. The reaction was monitored for completion by TLC. After completion of the reaction, the reaction mixture was diluted with water (10 mL) and cooled to 20-30° C. To the clear solution, dichloromethane (30 mL) was added and the mixture was stirred well at 20-30° C. 10N NaOH (1.2 g) solution was added and the bi-layer pH was adjusted to 9-9.5 using 25% potassium carbonate solution (final pH 9.45) at 20-30° C. The reaction mass was saturated with sodium chloride (6.25 g) and stirred well for 15-20 min. The layers were separated and the aqueous layer was extracted with dichloromethane (30 mL). To the combined dichloromethane layer, 1.05 eq of nicotinic acid (1.56 g) was added and the reaction mixture was stirred well at 20-30° C. for 0.5 to 1 h whereupon 1.5 eq of water was charged to the reaction mass and it was stirred for a

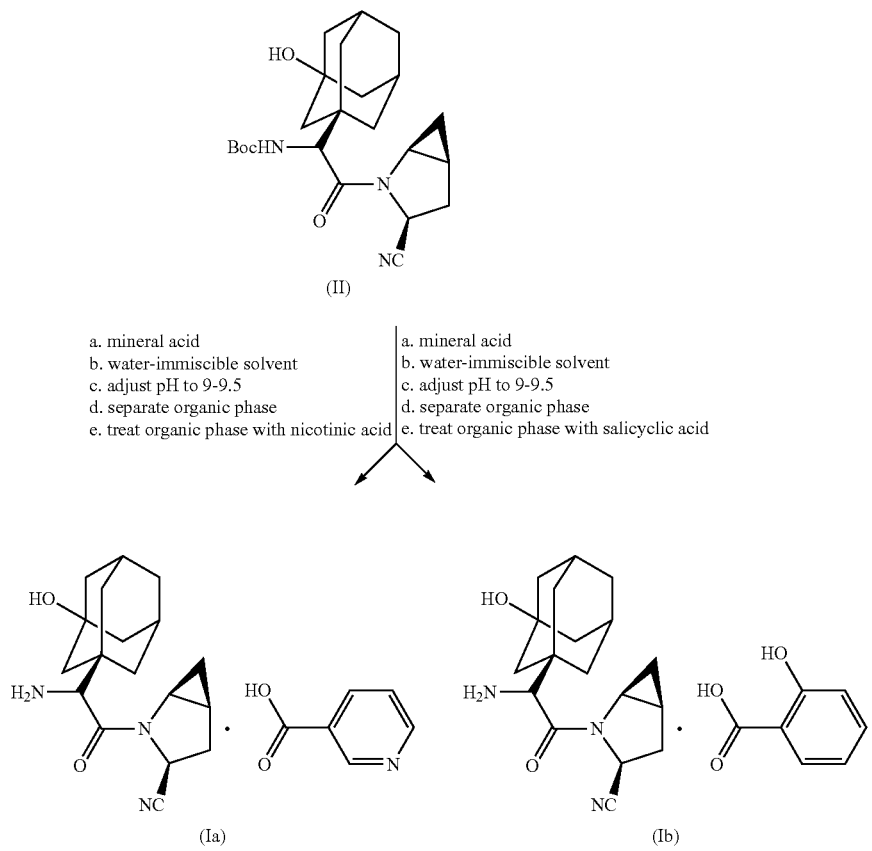

EXAMPLES

The following examples are illustrative of some of the embodiments of the invention described herein. These examples should not be considered to limit the spirit or scope of the invention in any way.

further 3-5 h at 20-30° C. The solid Saxagliptin nicotinate was filtered, washed with dichloromethane (10 mL), and dried. The damp material was dried in an oven at NMT 45° C. under vacuum for 4-5 h. (Yield: 69%; HPLC Purity=99.39%)

$^1$H NMR (CD$_3$OD, 300 MHz) δ (ppm): 0.85-0.87 (m, 1H), 0.93-1.02 (q, 1H, J=6 Hz), 1.51-1.73 (m, 12H), 1.80-

1.94 (m, 1H), 2.17-2.24 (m, 3H), 2.36-2.50 (m, 1H), 3.76-3.85 (m, 1H), 4.17 (s, 1H), 5.04-5.08 (dd, 1H, J=9 Hz, 3 Hz), 7.36-7.41 (m, 1H), 8.19-8.26 (2t, 1H, J=3 Hz), 8.49-8.51 (dd, 1H, J=6 Hz, 3 Hz), 8.96-8.97 (m, 1H).

$^{13}$C NMR (CD$_3$OD, 75 MHz) δ (ppm): 14.4, 19.2, 31.4, 31.5, 31.5, 36.0, 38.2, 38.2, 39.3, 41.0, 44.8, 44.9, 46.7, 46.9, 60.1, 68.7, 120.5, 124.8, 133.4, 138.9, 151.1, 151.7, 168.3, 171.3.

Moisture content (by Karl-Fischer method): 4.3%.

Example 2: Preparation of Saxagliptin Nicotinate (Ia)

To a well-stirred mixture of 10 g of (S)—N-Boc-3-hydroxyadamantylglycine-L-cis-4,5-methanoprolinenitrile (II) in 30 mL water, 1.4 eq of conc. HCl was added at NMT 30° C. and the reaction mixture was heated to 60-65° C. The reaction mass was maintained at this temperature for 2-3 h. After reaction completion (TLC), the reaction mixture was diluted with 20 mL water and cooled to 20-30° C. Dichloromethane (60 mL) was added to the solution which was stirred well at 20-30° C. 10N NaOH solution was added and the bi-layer pH adjusted to 9-9.5 using 25% potassium carbonate solution (final pH 9.3) at 20-30° C. The reaction mass was saturated with 12.5 g of sodium chloride and stirred well for 15-20 min. The layers were separated and the aqueous layer extracted with 60 mL of dichloromethane. To the combined dichloromethane layer, 1.05 eq of nicotinic acid (3.12 g) was added and the reaction mixture was stirred at 20-30° C. for 0.5 to 1 h. 1.5 eq of water was charged to the reaction mass and stirred for 3-5 h at 20-30° C. The solid Saxagliptin nicotinate was filtered and washed with 20 mL of dichloromethane and suction dried. The damp material dried in oven at NMT 45° C. under vacuum for 4-5 hrs. (Yield: 80%; purity: HPLC purity=99.51%).

The Saxagliptin nicotinate obtained in this example is substantially the same as the sample obtained in Example-1 above.

Example 3: Preparation of Saxagliptin Salicylate (Ib)

To a well-stirred mixture of 5 g of (S)—N-Boc-3-hydroxyadamantylglycine-L-cis-4,5-methanoprolinenitrile (II) in water (5 mL) was added isopropyl alcohol (5 mL) at 30° C., followed by 1.4 equivalents of conc. HCl and the reaction mixture was heated to 60-65° C. The reaction mixture was maintained at this temperature for 1.5-2 h. After completion of the reaction (TLC), the reaction mixture was diluted with water (10 mL) and cooled to 20-30° C. Dichloromethane (25 mL) was added to the solution which was stirred well at 20-30° C. 10N NaOH (1.2 g) solution was added and the bi-layer pH was adjusted to 9-9.5 using 25% potassium carbonate solution at 20-30° C. The reaction mixture was saturated with sodium chloride (7.5 g) and stirred well for 15-20 min. The layers were separated and the aqueous layer was extracted with dichloromethane (30 mL). To the combined dichloromethane layer, 1.05 eq of salicylic acid was added and the reaction mixture was stirred well at 20-30° C. for 2.5-3 h. The solid Saxagliptin salicylate was filtered and washed with dichloromethane (20 mL) and dried. (Yield: 77%; HPLC Purity=99.20%)

$^1$H NMR (DMSO-d$_6$, 300 MHz) δ (ppm): 0.72-0.75 (m, 1H), 0.98-1.05 (q, 1H, J=6 Hz), 1.47-1.69 (m, 12H), 1.81-1.89 (m, 1H), 2.15-2.27 (m, 3H), 2.35-2.45 (m, 1H), 4.01-4.04 (m, 1H), 4.23 (s, 1H), 5.12-5.16 (dd, 1H, J=9 Hz, 3 Hz), 6.62-6.68 (m, 2H), 7.16-7.22 (m, 1H), 7.66-7.82 (dd, 1H, J=9 Hz, 3 Hz).

$^{13}$C NMR (DMSO-d$_6$, 75 MHz) δ (ppm): 12.9, 17.3, 29.4, 29.5, 29.9, 34.8, 36.6, 36.7, 37.7, 39.1, 44.1, 44.2, 45.1, 45.4, 57.8, 66.3, 115.8, 116.5, 119.3, 119.7, 130.0, 131.9, 162.1, 166.7, 172.2.

Moisture content (by Karl-Fischer method): 0.13%.

Example 4: X-Ray Powder Diffraction (XRPD) Analysis

The data were acquired on a PANanalytical X-pert Pro MPD diffractometer with fixed divergence slits and an X-Celerator RTMS detector. The diffractometer was configured in Bragg-Brentano geometry; data was collected over a 2θ range of 5 to 35 using CuK$_\alpha$ radiation at a power of 40 mA and 45 kV. CuK$_\beta$ radiation was removed using a divergent beam Nickel filter. A step size of 0.017 degrees was used. A step time of 20 seconds was used. Samples were rotated at 1 Hz to reduce preferred orientation effects. The samples were prepared by the back-loading technique.

Example 5: FT-Infrared Spectroscopy Method

FT-IR spectroscopy was performed with a Perkin-Elmer FT-IR spectrometer. For the production of KBr compacts approximately 3 mg of sample was powdered with 300 mg of KBr. The spectra were recorded in transmission mode ranging from 4000 to 400 cm$^{-1}$.

Example 6: Differential Scanning Calorimetry (DSC) Analysis

The DSC thermograms were collected on a Mettler-Toledo 822e instrument. Samples (1 to 3 mg) were weighed into a 40 μL aluminum pan and were crimped closed with an aluminum lid. The samples were analyzed under a flow of nitrogen (ca. 50 mL/min) at a scan rate of 10° C./minute, from 40 to 300° C.

Example 7: $^1$H Nuclear Magnetic Resonance Spectroscopy

The $^1$H NMR spectra were recorded on a Bruker 300 MHz instrument. The sample (5-10 mg) was dissolved in deuterated solvent and the spectrum was recorded for 0-15 δ value.

Example 8: $^{13}$C Nuclear Magnetic Resonance Spectroscopy

The $^{13}$C NMR spectra were recorded on a Bruker 300 MHz instrument at a field of 75 MHz. The sample (5-10 mg) was dissolved in deuterated solvent and the spectrum was recorded for 0-200 δ value.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A salt of Saxagliptin of formula (I):

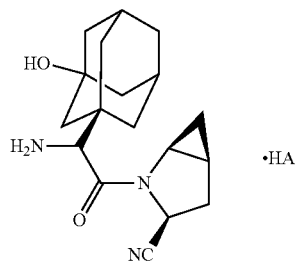

(I)

wherein HA is

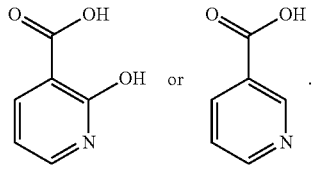 [SMILES: O=C(O)c1cccnc1O ; O=C(O)c1cccnc1]

2. The salt of claim 1 wherein the salt is crystalline.
3. Saxagliptin nicotinate of formula (Ia):

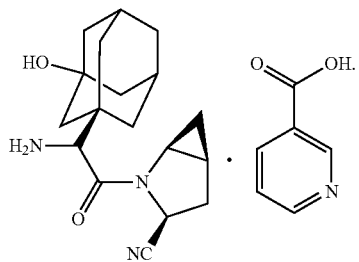

(Ia)

4. The Saxagliptin nicotinate (Ia) according to claim 3 in a crystalline monohydrate form.
5. The Saxagliptin nicotinate (Ia) according to claim 3 characterized by a XRPD diffractogram having peaks, expressed in degrees 2 theta, at approximately 7.3, 10.9, 16.3, 19.2, and 20.6.
6. The Saxagliptin nicotinate (Ia) according to claim 3 characterized by a XRPD diffractogram substantially similar to the XRPD diffractogram in FIG. 1.
7. The Saxagliptin nicotinate (Ia) according to claim 3 characterized by a DSC thermogram having two endothermic peaks with peak maxima at approximately 88° C. and approximately 235° C. and two exothermic peaks with peak maxima at approximately 140° C. and approximately 160° C.
8. The Saxagliptin nicotinate (Ia) according to claim 3 characterized by a DSC thermogram substantially similar to the DSC thermogram in FIG. 3.
9. The Saxagliptin nicotinate (Ia) according to claim 3 characterized by an IR spectrum having one or more adsorption peaks, expressed in cm$^{-1}$, at approximately 3336, 3046, 2134 and 1647.
10. The Saxagliptin nicotinate (Ia) according to claim 3 characterized by an IR spectrum substantially similar to the IR spectrum in FIG. 5.
11. Saxagliptin salicylate of formula (Ib):

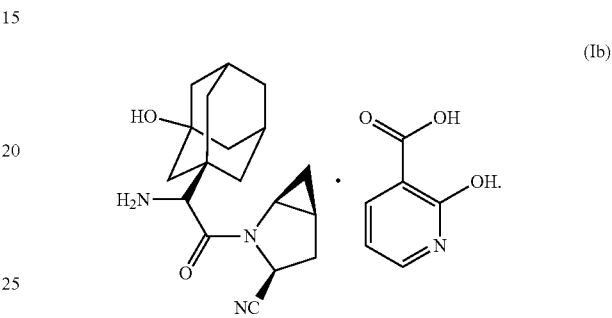

(Ib)

12. The Saxagliptin salicylate (Ib) according to claim 11 in an anhydrous crystalline form.
13. The Saxagliptin salicylate (Ib) according to claim 11 characterized by a XRPD diffractogram having peaks, expressed in degrees 2 theta, at approximately 6.7, 8.4, 13.4, 15.1, 17.5, and 21.1.
14. The Saxagliptin salicylate (Ib) according to claim 11 characterized by a XRPD diffractogram substantially similar to the XRPD diffractogram in FIG. 2.
15. The Saxagliptin salicylate (Ib) according to claim 11 characterized by a DSC thermogram having an exothermic peak with a peak maximum at approximately 210° C. and an endothermic peak with a peak maximum at approximately 263° C.
16. The Saxagliptin salicylate (Ib) according to claim 11 characterized by a DSC thermogram substantially similar to the DSC thermogram in FIG. 4.
17. The Saxagliptin salicylate (Ib) according to claim 11 characterized by an IR spectrum having one or more adsorption peaks, expressed in cm$^{-1}$, at approximately 3584, 3455, 3041.8, 2112, 1669 and 1630.
18. The Saxagliptin salicylate (Ib) according to claim 11 characterized by an IR spectrum substantially similar to the IR spectrum in FIG. 6.
19. A process for the preparation of salts of Saxagliptin of formula I:

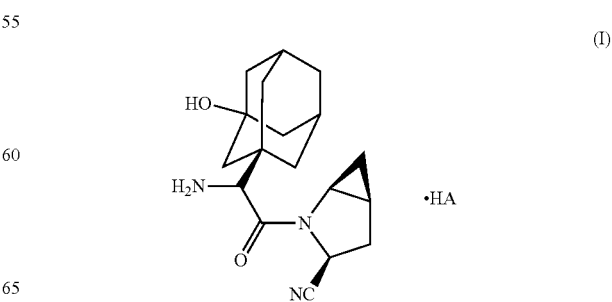

(I)

wherein HA is

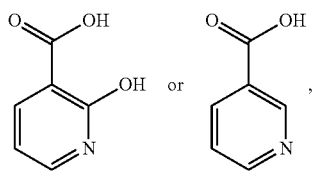 [SMILES: O=C(O)c1cccnc1O ; O=C(O)c1cccnc1]

the process comprising:
(a) treating, at a temperature of about 40° C. to about 65° C., (S)—N-Boc-3-hydroxyadamantylglycine-L-cis-4,5-methanoprolinenitrile with a mineral acid in either: (i) water or (ii) a mixture of water and an alcoholic solvent, thereby forming a solution;
(b) adding a water-immiscible solvent to the solution, thereby forming a bi-phasic solution;
(c) basifying the bi-phasic solution by adjusting the pH to about 9 to about 9.5, thereby forming a basified bi-phasic solution;
(d) separating an organic phase from the basified bi-phasic solution;
(e) treating the organic phase with an organic acid selected from salicylic acid and nicotinic acid, thereby forming a treated organic phase; and
(f) isolating the salt of Saxagliptin from the treated organic phase.

20. The process according to claim 19 wherein the mineral acid is hydrochloric acid.

21. The process according to claim 19 wherein the alcoholic solvent is a $C_1$-$C_3$ alkanol selected from the group consisting of methanol, ethanol, and isopropanol.

22. The process according to claim 19 wherein the water-immiscible solvent is dichloromethane or ethyl acetate.

23. The process of claim 19, wherein the organic acid is nicotinic acid, and the salt of Saxagliptin of formula (I) is Saxagliptin nicotinate characterized by a XRPD diffractogram having peaks, expressed in degrees 2 theta, at approximately 7.3, 10.9, 16.3, 19.2, and 20.6.

24. The process of claim 19, wherein the organic acid is salicylic acid, and the salt of Saxagliptin of formula (I) is Saxagliptin salicylate characterized by a XRPD diffractogram having peaks, expressed in degrees 2 theta, at approximately 6.7, 8.4, 13.4, 15.1, 17.5, and 21.1.

25. The process of claim 19, wherein the organic acid is nicotinic acid, and the salt of Saxagliptin of formula (I) is Saxagliptin nicotinate having a HPLC purity of at least 99.39%.

* * * * *

UNITED STATES PATENT AND TRADEMARK OFFICE
CERTIFICATE OF CORRECTION

PATENT NO. : 9,994,523 B2  
APPLICATION NO. : 14/403552  
DATED : June 12, 2018  
INVENTOR(S) : Padiyath Mohammed Akbarali et al.

Page 1 of 2

It is certified that error appears in the above-identified patent and that said Letters Patent is hereby corrected as shown below:

In the Specification

Column 4, Lines 12-17, delete " 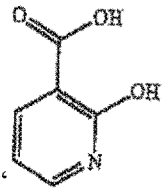 " and insert -- 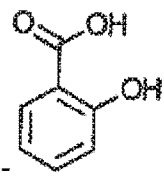 --

Column 5, Lines 3-8, delete " 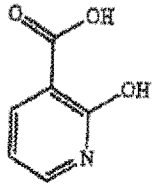 " and insert -- 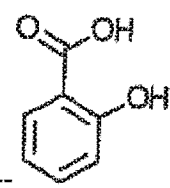 --

Column 7, Lines 12-17, delete " 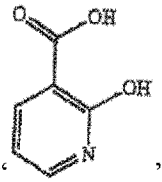 " and insert -- 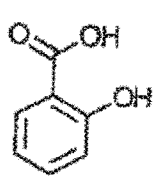 --

Column 8, Lines 5-10, delete " 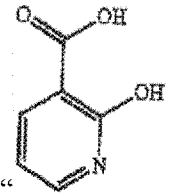 " and insert -- 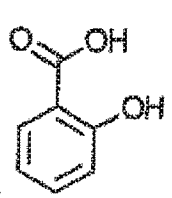 --

Signed and Sealed this  
Thirtieth Day of October, 2018

Andrei Iancu  
*Director of the United States Patent and Trademark Office*

CERTIFICATE OF CORRECTION (continued)
U.S. Pat. No. 9,994,523 B2

Column 8, Lines 55-60, delete " 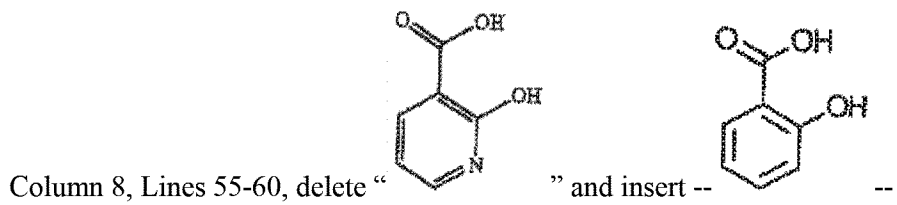 " and insert -- --

In the Claims

Column 13, Lines 30-39, Claim 1, delete " 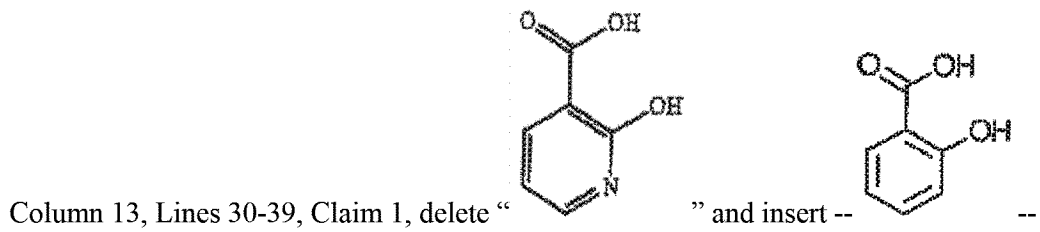 " and insert -- --

Column 14, Lines 17-23, Claim 11, delete " 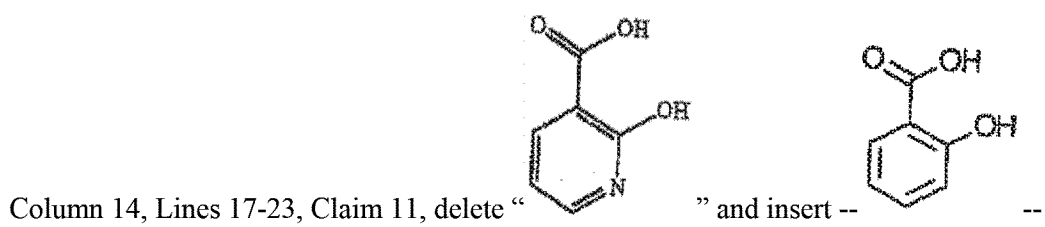 " and insert -- --

Column 15, Lines 2-9, Claim 19, delete " 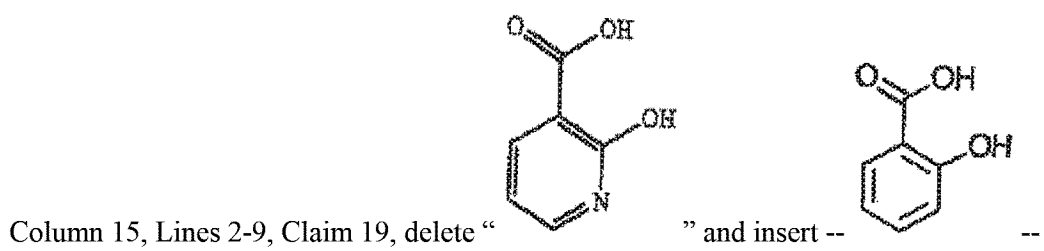 " and insert -- --